(12) United States Patent
Adhikari et al.

(10) Patent No.: US 9,856,500 B2
(45) Date of Patent: Jan. 2, 2018

(54) METHOD OF CONSOLIDATED BIOPROCESSING OF LIGNOCELLULOSIC BIOMASS FOR PRODUCTION OF L-LACTIC ACID

(71) Applicant: Council of Scientific and Industrial Research, New Delhi (IN)

(72) Inventors: Dilip Kumar Adhikari, Mohkampur (IN); Jayati Trivedi, Mohkampur (IN); Deepti Agrawal, Mohkampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 201 days.

(21) Appl. No.: 14/415,652

(22) PCT Filed: Jul. 17, 2013

(86) PCT No.: PCT/IN2013/000443
§ 371 (c)(1),
(2) Date: Jan. 19, 2015

(87) PCT Pub. No.: WO2014/013509
PCT Pub. Date: Jan. 23, 2014

(65) Prior Publication Data
US 2015/0197777 A1    Jul. 16, 2015

(30) Foreign Application Priority Data
Jul. 19, 2012 (IN) ............................ 2237/DEL/2012

(51) Int. Cl.
| | | |
|---|---|---|
| *C12P 7/56* | (2006.01) |
| *C02F 3/30* | (2006.01) |
| *C12N 1/20* | (2006.01) |
| *C12R 1/01* | (2006.01) |
| *B09C 1/10* | (2006.01) |

(52) U.S. Cl.
CPC ................. *C12P 7/56* (2013.01); *C12N 1/20* (2013.01); *C12R 1/01* (2013.01); *C12P 2203/00* (2013.01)

(58) Field of Classification Search
CPC .......... C12N 1/20; C12P 2203/00; C12P 7/56; C12R 1/01; Y10S 435/911; B01J 2220/4825
USPC ......... 435/254.1, 262.5, 911, 29, 32, 34, 41, 435/139
IPC .................. B09C 1/10; C02F 3/30; C12P 7/56
See application file for complete search history.

(56) References Cited

U.S. PATENT DOCUMENTS

2005/0106694 A1*  5/2005  Green ..................... C12R 1/07
                                                    435/146

FOREIGN PATENT DOCUMENTS

| AU | WO 2007140521 A1 * | 12/2007 | ............... A61K 8/97 |
| WO | WO 2012/071392 A2 * | 5/2012 | ............... C12N 1/21 |
| WO | WO-2014/013509 | 1/2014 | |

OTHER PUBLICATIONS

Taxonomy Paenibacillus macerans (Bacillus macerans) (Species Paema Taxon Identifier http://www.uniprot.org/taxonomy/44252 printed Sep. 29, 2016.*
Nakamura et al. 1988. Taxonomic Study of Bacillus coagulans Hammer 1915 with a Proposal for *Bacillus smithii* sp. nov. International Journal of Systematic Bacteriology, vol. 38, pp. 63-73.*
Ryckeboer et al. 2003. Microbiological aspects of biowaste during composting in a monitored compost bin. Journal of Applied Microbiology, vol. 94, 127-137.*
Partanan et al 2010. Bacterial diversity at different stages of the composting process. BMC Microbiology vol. 10, pp. 94-104 (1-11).*
Sigma-Aldrich, 2 pages. http://www.sigmaaldrich.com/catalog/search?term=carboxymethylcellulose&interface=All; Printed Mar. 15, 2017.*
Kadam et al. 2003. Availability of corn stover as a sustainable feedstock for bioethanol production. Bioresource Technology, vol. 88, pp. 17-25.*
"International Application No. PCT/IN2013/000443, International Search Report dated Nov. 28, 2013", (dated Nov. 28, 2013), 4 pgs.

* cited by examiner

*Primary Examiner* — Pablo S Whaley
*Assistant Examiner* — Kailash C Srivastava
(74) *Attorney, Agent, or Firm* — Schwegman Lundberg & Woessner, P.A.

(57) ABSTRACT

The present invention pertains to a method for consolidated bio processing of lignocellulosic biomass to L-Lactic acid. Particularly, the present invention relates to the production of L-Lactic Acid from low cost non edible feedstock lignocellulosic biomass. More particularly the present invention relates to the process for one step production of L-Lactic Acid from lignocellulosic biomass using thermophilic bacteria *Paenibacillus macerans* IIPSP3 (MTCC 5569), which is not only capable of hydrolyzing cellulose to glucose but also further fermenting it to L-Lactic Acid under aerobic conditions, without any growth inhibition in presence of lignin. The present invention provides a process which has less chances of contamination, as the fermentation is carried out at higher temperatures and is economically attractive, as preferably no external enzyme loadings are required.

11 Claims, 2 Drawing Sheets

METHOD OF CONSOLIDATED BIOPROCESSING OF LIGNOCELLULOSIC BIOMASS FOR PRODUCTION OF L-LACTIC ACID

PRIORITY CLAIM TO RELATED APPLICATIONS

This application is a U.S. national stage application filed under 35 U.S.C. §371 from International Application Serial No. PCT/IN2013/000443, which was filed Jul. 17, 2013, and published as WO 2014/013509 on Jan. 23, 2014, and which claims priority to India Application No. 2237/DEL/2012, filed Jul. 19, 2012, which applications and publication are incorporated by reference as if reproduced herein and made a part hereof in their entirety, and the benefit of priority of each of which is claimed herein.

FIELD OF THE INVENTION

The present invention pertains to a method for consolidated bio processing of lignocellulosic biomass to L-Lactic acid. Particularly, the present invention relates to the production of L-Lactic Acid from low cost non edible feedstock lignocellulosic biomass. More particularly the present invention relates to the process for one step production of L-Lactic Acid from lignocellulosic biomass using thermophilic bacteria Paenibacillus macerans IIPSP3 (MTCC 5569), having been deposited under accession number MTCC 5569 on Jun. 28, 2010 under the Budapest Treaty at Microbial Type Culture Collection & Gene Bank, Institute of Microbial Technology, Sector 39-A, Chandigarh 160 036 India, which is not only capable of hydrolysing cellulose to glucose but also further fermenting it to L-Lactic Acid under aerobic conditions, without any growth inhibition in presence of lignin.

It is further appreciated that the process has less chances of contamination, as the fermentation is carried out at higher temperatures and is economically attractive, as preferably no external enzyme loadings are required.

BACKGROUND OF THE INVENTION

Lactic Acid or 2-Hydroxypropionic Acid has wide applications in diverse areas like food, pharmaceuticals, cosmetics, green solvents, specialty chemicals, textile, leather and biodegradable plastics/polymers. Other potential applications include biocompatible polylactic acids for biomedical applications.

On account of its eco-friendliness, easy recyclability and cost effectiveness, the demand for lactic acid based biopolymers has increased, thereby increasing the lactic acid consumption. It has been projected that the global demand for lactic acid would reach 328.9 thousand metric tons by year 2015.

At present, fermentation of sugars by lactic acid bacteria supplies all the optically pure lactic acid produced worldwide. However, industrial lactic acid production by fermentation starts with glucose derived from starch or sucrose, derived from food-based materials. One of the most critical and lucrative areas of interest at present is the production of L(+)-lactic acid from non edible and cheaper sources such as lignocellulosic biomass.

Several reports are available wherein the lactic acid is generated by fermentation of renewable agricultural feedstock resources such as corn, whey, potatoes, cane sugar, molasses of beet sugar, xylose stream generated from lignocellulosic biomass etc.

U.S. Pat. No. 4,963,486 issued to Hang, on Oct. 16, 1990 claims the production of L (+) lactic acid from Rhizopus oryzae as a single step fermentation process from renewable biomass namely corn, cassava, rice, oat, wheat, barley and sorghum representing starchy biomass. The patent claims that the fungus mentioned in the invention is capable of supplying all the required enzymes for both saccharification of gelatinised starch and fermentation to L (+)-lactic acid. Hang also discloses the production of 350 g of L (+)-lactic acid from one kg crushed corn.

Similarly Tsai et al in their U.S. Pat. No. 5,464,760 (7 Nov. 1995) claim the production of lactic acid using a consortium of Lactobacillus strains from Starch under SSF conditions in combination with α-amylase enzyme and thereafter its recovery in pure form from Sodium lactate using various methods like electro-dialysis. The invention of U.S. Pat. No. 5,464,760 involves the bioconversion of industrial food waste, such as potato waste, corn, rice, cheese whey, cane sugars, beet sugars or the like, containing starch to lactic acid suitable for conversion to photodegradable or biodegradable plastics.

The European Patent Application filed by Shimadzu Corporation (EP0770684A2) with a priority date of 27 Oct. 1995, claims the production of L-Lactic Acid with a purity of more than 70% to as high as 95% by Bacillus species in particular under anaerobic conditions mainly from glucose, sucrose, maltose, fructose, mannitol, lactose and Starch.

Numerous papers and patents have reported the production of L(+)-lactic acid through simultaneous saccharification and fermentation (SSF) route. However one of the major disadvantage quoted by Hofvendahl and Hahn-Hagerdal (Enzyme Microb. Technol., 2000; 26: 87-107) with the SSF process is the difference in the optimal conditions for enzymatic hydrolysis (pH<5.0 and temperature: 50° C.) and lactic acid fermentation (pH-5.0-7.0 and temperature being 37-43° C.).

Shin-ichiro Abe and Motoyoshi Takagi have shown the production of lactic acid using a combination of Trichoderma reesei as a source of cellulase enzyme for saccharification and Lactobacillus delbrueckii as the lactic acid producing microorganism. At the end of 120 hours 52.5 g/L of lactic acid was produced with only 6.2 g/L of reducing sugar left with an initial feed of 100 g/L of cellulose powder Type C (Biotechnol. Bioengg; 1991, 37: 93-96).

R. P. John et al (Braz. Arch. Biol. Technol.; 2008, 51 (6): 1241-1248) have also reported the production of L-lactic acid from cassava starch through SSF route using combination of L. delbrueckii and L. casei strain together with use of α-amylase and glucoamylase enzyme.

Mark S. Ou et al (J Ind Microbiol Biotechnol; 2011, 38:599-605) have also reported to produce L(+) Lactic Acid with 80% yield under fed batch SSF conditions of crystalline Cellulose with fungal enzymes dosed at 15 FPU/g Cellulose and Bacillus coagulans at pH-5 and temperature being 50° C.

In yet another patent application, Otto has claimed (US 2004/0203122 A1 and WO 2004/063382A2) the preparation of Lactic Acid through homolactic fermentation by a moderate thermophile of Bacillus under anaerobic conditions from glucose, xylose and arabinose derived from Biomass and grown in chemically defined medium.

Van Walsum et al in their Patent Application US 2011/0183389 have claimed the conversion of xylose to Lactic Acid from woody biomass which is prehydrolysed by acid or enzyme to generate an aqueous extract comprising of glucose, mannose, galactose, xylose and arabinose using *Bacillus coagulans* strain.

Very recently Direvo Industrial Biotechnology in their patent application WO 2013050584 A1 published on 11 Apr. 2013 has claimed the bioconversion of lignocellulosic biomass to Lactic acid. However, as per their claims the pretreatment step not only involves mechanical disprution using ball milling, but also physical pretreatment that involves use of steam, sulphuric acid, alkali but also biochemical step involving use of cellulose and hemicellulose degrading enzymes. The claimed thermophilic and xylanolytic bacteria *Thermoanaerobacter* is able to ferment the hydrolyzed lignocellulosic biomass under obligate anaerobic conditions with major product as L-lactic acid and acetic acid as by-product.

In the recent past, the conversion of cellobiose, to lactic acid has gained lot of importance. Adsul et al (AEM, August 2007, p. 5055-5057) have reported the production of 90 g/L L(+) Lactic Acid from 100 g/L of Cellobiose from a mutant strain of *Lactobacillus delbrueckii* showing aryl-β-glucosidase activity from whole cells, thereby suggesting that the enzyme is cell bound. This strain is known to utilize even cellotriose also efficiently.

Recently Mohamed Ali Abdel-Rahman et at (Appl Microbiol Biotechnol (2011) 89:1039-1049) have reported the production of optically pure L (+) Lactic Acid (~35 g/L) when fed with cellobiose and glucose (20 g/L each) simultaneously at the end of 15 hours from *Enterococcus mundtii* QU 25 grown at 43° C. at pH-7.0.

Pratibha Dheeran et al (J Ind Microbiol Biotechnol; DOI 10.1007/s10295-012-1093-1) have described the xylanolytic activity of *Paenibacillus macerans* IIPSP3 (MTCC 5569) obtained from termite gut and its growth of various carbon sources, such as birchwood xylan, beechwood xylan, oatspelt xylan, carboxymethyl cellulose, cellobiose, glucose, xylose, and raw substrates, such as bagasse (untreated and pre-treated with 0.1% $H_2SO_4$ at 121° C. for 30 min), and corn cob chips (collected from nearby farms), at concentrations ranging from 0.1 to 2.5% (w/v). However they fail to report the lactic acid production from the isolated strain.

Thus none of the papers and the patents in the state of art, taken in combination or singly describes the process for a direct conversion of lignocellulosic biomass to L (+)-lactic Acid by thermophilic *Paenibacillus macerans* without any addition of external enzyme such as amylases or cellulases or their combination, that too under aerobic conditions.

Thus there is a need in the art for thermo-tolerant organisms capable of not only hydrolysing the cellulose rich lignocellulosic biomass, but also efficiently producing value added product such as L-lactic acid in a single step process. The present invention meets all these needs.

The present invention offers consolidated bio-processing of lignocellulosic biomass to L-Lactic Acid wherein the novel thermophilic strain of *Paenibacillus* IIPSP3 not only attacks the glucan and xylan, the principal constituents of biomass and breaks them of monomeric sugars but is also capable of fermenting these sugars to L-Lactic Acid under aerobic conditions. The cellulolytic activity of *Paenibacillus macerans* IIPSP3 (MTCC 5569) has been proven by fermentation of pure cellulosic substrates such as sodium salt of carboxy methyl cellulose, micro-crystalline cellulose, Avicel PH 101 and cellobiose to L-Lactic Acid.

OBJECTIVES OF THE INVENTION

The main objective of the invention is to provide a method for consolidated bio processing of lignocellulosic biomass to L-Lactic acid in a single step that combines hydrolysis and fermentation by *Paenibacillus macerans* IIPSP3 (MTCC 5569), which obviates the drawbacks of hitherto known methods as detailed above.

Another objective of the present invention is to provide a simple efficient process wherein the hydrolysis and fermentation both can be performed at the same temperature that is 50° C.

Yet another objective of the preset invention is to provide a process wherein no strict anaerobic conditions are required for the fermentation of products derived from lignocellulosic biomass to optically pure L (+)-Lactic acid.

Still another objective of the present invention is to provide a cost effective process wherein preferably no external enzymes are used.

Yet another objective of the present invention is to obtain a product which is optically Pure L (+) Lactic Acid and no other by-product is being formed.

SUMMARY OF THE INVENTION

Accordingly, the present invention provides a method of consolidated bioprocessing of pre-treated lignocellulosic biomass, synthetic cellulosic substrates and their derivatives to L(+)-lactic acid and/or lactate using a thermophilic and cellulolytic bacterial strain *Paenibacillus macerans* IIPSP3 (MTCC 5569); wherein process steps comprising:
a. sterilizing fermentation medium at a temperature in the range of 100-121° C., wherein the said fermentation medium comprising:
   i. Carbon source
   ii. Ammonium sulphate
   iii. Yeast Extract
   iv. Magnesium chloride
   v. Calcium chloride
   vi. Trace metals
b. inoculating the said fermentation medium with microbial culture, wherein the said microbial culture is a Gram positive thermophilic and cellulolytic bacterial isolate *Paenibacillus macerans* IIPSP3 (MTCC 5569);
c. incubating the said fermentation medium at a temperature in the range of 40-55° C.
d. adding sterile neutralizing agent to the said fermentation medium in the range of 4-8 hours of incubation to maintain pH of the medium in the range of about 5.5-7.2.

In an embodiment of the present invention, the carbon source is selected from the group consisting of lignocellulosic biomass, Avicel PH-101, microcrystalline cellulose (MCC), sodium salt of carboxymethyl cellulose (Na Salt if CMC), beechwood xylan, simple sugars like glucose, cellobiose, xylose.

In another embodiment of the present invention, the lignocellulosic biomass is selected from the group consisting of agricultural residue, forest residue, herbaceous material, waste paper, paper, paper pulp, paper mill residue.

In yet another embodiment of the present invention, the agricultural residue is selected from the group consisting of bagasse obtained from sweet sorghum, corn stover and sugarcane, cotton stalks, rice straw, wheat straw.

In still another embodiment of the present invention, the synthetic cellulosic substrates and their derivatives is selected from the group consisting of Avicel PH-101, microcrystalline cellulose, sodium salt of carboxymethyl cellulose, cellobiose and glucose.

In still another embodiment of the present invention, the trace metal is selected from the group consisting of $Na_2EDTA$, $MnSO_4.4H_2O$, $(NH_4)_6Mo_7O_{24}.4H_2O$, $FeSO_4.7H_2O$, $CoCl_2.6H_2O$, $NiCl_2.6H_2O$, $ZnSO_4.7H_2O$.

In yet another embodiment of the present invention, the neutralizing agent is selected from the group consisting of sodium hydroxide, calcium hydroxide, calcium carbonate.

In still another embodiment of the present invention, the process carried out in a single bioreactor under aerobic conditions and can be performed in batch and fed-batch conditions.

In yet another embodiment of the present invention, the lignocellulosic biomass, synthetic cellulosic substrates and their derivatives are contacted with *Paenibacillus macerans* IIPSP3 (MTCC 5569) for a period of 6-48 hours.

In still another embodiment of the present invention, no external enzymes are used during the process for the production of Lactic Acid.

DETAILED DESCRIPTION OF THE INVENTION

Figure 1:
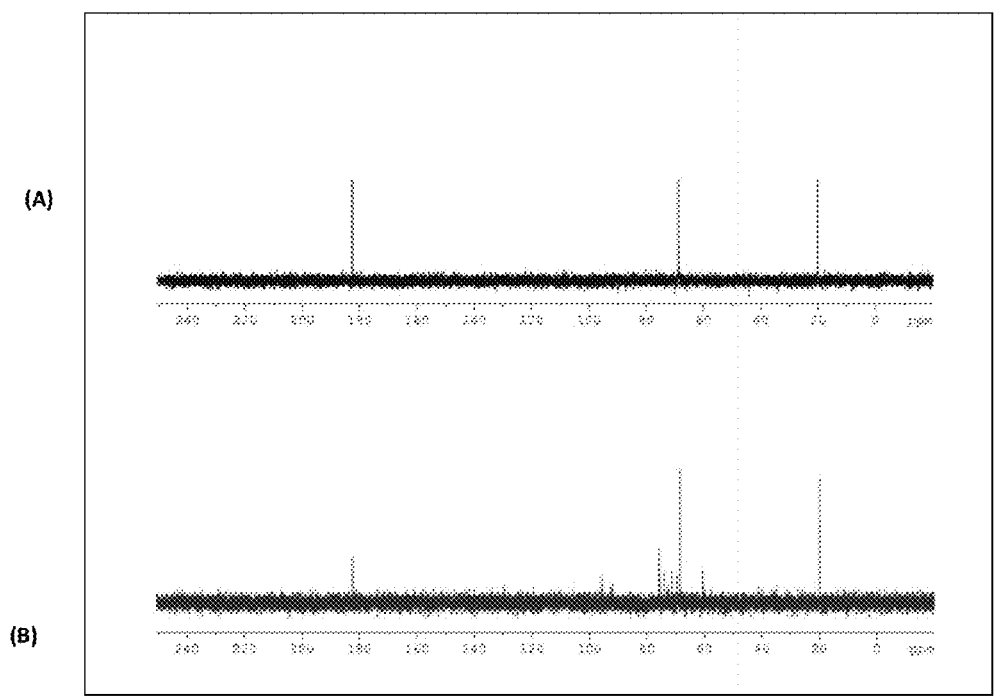
FIG. 1 shows 13 C NMR spectra for A) Calcium L(+) lactate as reference sample B) Fermentation broth as test sample.

Accordingly the present invention offers a consolidated bioprocess for the production of L (+)-lactic acid from cellulose rich lignocellulosic biomass using a novel thermophile *Paenibacillus macerans* IIPSP3 (MTCC 5569). This strain was isolated from termite gut collected from CSIR-IIP Campus, Dehradun, India.

The strain was identified as *Paenibacillus macerans* based on its 16S rRNA gene sequence (1,478 bp), which was aligned with sequences available in the NCBI database using ClustalX software, and further named as *P. macerans* IIPSP3. The phylogenetic tree clearly showed that the isolated strain had more than 90% homology with the strain *P. macerans*. The 16S rRNA gene sequence has been deposited in the Gene Bank under the accession no. HM246634.1 and an IDA deposit has been made to MTCC, Institute of Microbial Technology, Chandigarh, India (MTCC 5569).

The medium under which the consolidated bioprocessing by *Paenibacillus macerans* IIPSP3 (MTCC 5569) was carried out, consist of 20 g/L of carbon source, 2 g/L yeast extract, 2 g/L ammonium sulphate in phosphate buffered medium with 0.2 g/L magnesium chloride and 0.025 g/L calcium chloride. This medium was further fortified with 2 g/L mineral solution. This mineral salt solution was composed per liter of 0.4 g of $Na_2EDTA$, 0.34 g of $MnSO_4.4H_2O$, 0.40 g of $(NH_4)_6Mo_7O_{24}.4H_2O$, 0.8 g $FeSO_4.7H_2O$, 0.04 g $CoCl_2.6H_2O$, 0.02 g $NiCl_2.6H_2O$, 0.02 g $ZnSO_4.7H_2O$.

In the present case, the carbon source could be microcrystalline cellulose (MCC), sodium salt of carboxymethyl cellulose (Na salt of CMC), lignocellulosic biomass, waste paper, paper and pulp and paper mill residue etc. Alternatively, simple sugars like glucose, xylose and cellobiose could also serve as carbon source.

The said biomass used in the present invention was obtained by acid pretreatment of various lignocellulosic sources such as forest residues, herbaceous material, agricultural residues (bagasse derived from sugarcane, sweet sorghum, corn stover, cassava), straw derived from rice and wheat, cotton stalks etc. This acid pretreatment at high temperature solubilised most of the hemicellulose thus facilitating the accessibility of cellulose rich fraction to cellulolytic enzymes secreted by *Paenibacillus macerans* IIPSP3 (MTCC 5569).

When complex carbon substrates such as lignocellulosic biomass, sodium salt of carboxymethyl cellulose, MCC, waste paper were used for consolidated bioprocessing to lactic acid, the endoglucanase assay in the crude supernatant was performed by measuring the initial rate of hydrolysis of 1% carboxymethyl cellulose sodium salt in the range of linear increase of reducing sugar (RS) concentration over time in 50 mM sodium acetate buffer pH 4.8 at 50° C. Hydrolysis was carried out without stirring for 10 minutes followed by termination of reaction using 3 ml of DNS reaction.

One IU is defined as the moles of glycosidic bonds hydrolysed in one minute during initial hydrolysis. Crude extracts were diluted so as to give a linear relationship between enzyme concentration and activity measured. Carboxymethyl cellulose (Fluka Grade: 21902) with an average degree of substitution (DS) of 0.77 was used as a substrate.

The cellobiase or the β-glucosidase activity was measured in the culture supernatant as per the IUPAC protocol by T. K. Ghosh (1987).

The temperature at which the fermentation was carried out is 50° C. The initial pH of the medium was in the range of 7.2-7.5 and during the entire course of process, the conditions were aerobic. As the lactic acid production proceeded there was a drop in the pH of the medium. A pH of less than 4.8 inhibited the growth of the organism thereby cessing the production of lactic acid. Therefore the pH was maintained above 5.5 (using $CaCO_3$) so as to prevent the inhibition due to lactic acid production and thereby maintaining *Paenibacillus* cells in their growth phase for its continuous production.

The said process can run under batch and fed batch conditions. Conventional methods like adsorption, electrodialysis, membrane separation, reactive extraction can be adopted for the recovery and concentration of lactic acid from the fermentation broth.

EXAMPLES

The following examples are given by the way of illustration and therefore should not be construed to limit the scope of the present invention.

Example 1: Production of L-Lactic Acid Using Glucose as Sole Carbon Source

Seed cultures of *Paenibacillus macerans* IIPSP3 (MTCC 5569) were grown aerobically at 50° C. in 100 ml Erlenmeyer Flask containing 20 ml medium with following composition (Table 1). Before inoculation of *Paenibacillus macerans* IIPSP3 (MTCC 5569), the said media was autoclaved at 121° C. for 15 min, with final pH value of 7.2±0.3. The carbon source in the said medium in this experiment was glucose.

TABLE 1

Medium Composition for growth of *Paenibacillus macerans* IIPSP3 (MTCC 5569) and fermentation

| Media Components | g/L |
|---|---|
| Carbon Source | 20 |
| Yeast Extract | 2 |
| $(NH_4)_2SO_4$ | 2 |
| $KH_2PO_4$ | 0.26 |
| $Na_2HPO_4 \cdot 7H_2O$ | 2.17 |
| $MgCl_2 \cdot 6H_2O$ | 0.2 |
| $CaCl_2$ (Fused) | 0.025 |
| Trace Metal Solution | 2 ml/L |
| Composition of Trace Metal Solution | |
| $Na_2EDTA$ | 0.4 |
| $MnSO_4 \cdot 4H_2O$ | 0.34 |
| $(NH_4)_6 Mo_7O_{24} \cdot 4H_2O$ | 0.4 |
| $FeSO_4 \cdot 7H_2O$ | 0.8 |
| $CoCl_2 \cdot 6H_2O$ | 0.04 |
| $NiCl_2 \cdot 6H_2O$ | 0.02 |
| $ZnSO_4 \cdot 7H_2O$ | 0.02 |

2 ml of Mid-log aliquot of seed culture was transferred to 100 ml of autoclaved fermentation medium placed in 500 ml capacity Erlenmeyer flask, with glucose as a sole carbon source. The lactic acid production was carried out at 50° C. & 120 rpm in Innova Incubator shaker Model No. 4430, under aerobic conditions. After 4 hours of incubation the pH dropped to 4.95. Three different strategies were followed. In one flask no pH was adjusted (A), in other flask the pH was maintained above 5.0 (B) whereas in yet another flask the pH was strictly maintained at 6.0 (C) using 5% sterile $Ca(OH)_2$.

The fermentation was carried out for 5 days and samples were withdrawn after every 24 hours under aseptic conditions. The samples were centrifuged down at 10,000 rpm for 5 min at 4° C. and the supernatant was analysed for L-lactic acid production and residual glucose using HPLC (Hi-Plex-H column: Agilent Technologies) as shown in Table 2. The mobile phase was 2 mM sulphuric acid with flow rate being 0.7 ml/min and oven temperature being 70° C. Lactic acid, as a fermentation product, was further reconfirmed via 1D $^1$H-NMR and 1D $^{13}$C-NMR spectroscopy.

This experiment confirmed that for continuous production of L(+) Lactic acid pH maintenance was essential. If the pH was not controlled the produced lactic acid proved detrimental for the growth of the organism and continuous production of lactic acid.

Example 2: Confirmation of End Product as L (+) Lactic Acid by NMR Studies

Lactic acid, as a fermentation product, was confirmed via 1D 1H-NMR and 1D 13C-NMR spectroscopy. Bruker Avance III 500 MHz spectrometer equipped with 5 nm BBO probe head, operating at 125.77 MHz and 50.13 MHz resonance frequency was used for obtaining 13C and 1H NMR spectra respectively. The conventional 13C NMR was carried out by reverse gated coupling mode using following parameters: NS=492, D1-5 sec. After neutralization of the fermentation broth with $CaCO_3$ L-Lactic acid existed in Calcium L-Lactate form in the broth, thus a 20% (w/v) solution of Calcium L-Lactate Hydrate in $D_2O$ was used for reference purpose.

The 13 C spectra of reference sample (pure calcium lactate) showed 3 peaks at 19.9 ppm, 68.3 ppm, 182.4 ppm which correspond to carbons present in functional groups —CH3, —CH—OH, —COO— respectively. The NMR spectra of fermentation broth sample also showed 3 major peaks at 20.15 ppm, 68.6 ppm, 182.5 ppm. A perfect overlap of major peaks between fermentation broth sample and pure calcium lactate as evident in FIG. 1, confirmed the production of lactic acid. Besides the major peaks some minor peaks in the region 60.5 ppm to 110 ppm were also visible in the fermentation broth sample which could be possibly due to the carbon atoms present in the carbohydrate.

Example 3: Effect of Neutralizing Agent on L-Lactic Acid Production Using Glucose as Sole Source of Carbon All the experimental conditions for the seed culture, production and analysis of end products were identical as mentioned in Example 1, except for the incubation time and use of neutralizing agent. Two different neutralizing agents were used to control pH of the medium, one being 5% sterile NaOH and other being 5% sterile $Ca(OH)_2$.

The present experiment was restricted to 24 hours only and the L-lactic acid formation is shown in Table 3.

TABLE 2

Effect of pH control on the productivity of L-Lactic Acid by *Paenibacillus macerans* IIPSP3 (MTCC 5569) fed with 2% glucose as carbon source.

| Hours of Incubation | Residual Glucose (mg/ml) | | | L(+)-lactic acid formed (mg/ml) | | |
|---|---|---|---|---|---|---|
| | Flask A | Flask B | Flask C | Flask A | Flask B | Flask C |
| 0 | 19.96 | 19.96 | 19.96 | 0.059 | 0.061 | 0.065 |
| 24 | 14.6 | 9.7 | 9.2 | 3.51 | 8.8 | 9.26 |
| 48 | 18.5 | 7.7 | 5.7 | 3.39 | 11.3 | 13.47 |
| 96 | 18 | 6.9 | 4.91 | 4.05 | 11.6 | 13.66 |
| 120 | 18.3 | 7.5 | 4.86 | 3.84 | 11.8 | 13.67 |

Note:
Flask A-No pH control;
Flask B-pH maintained above 5,
Flask C-pH maintained to 6.0.

TABLE 3

Effect of neutralizing agent on the productivity of L-Lactic Acid by *Paenibacillus macerans* IIPSP3 (MTCC 5569) fed with 2% glucose as carbon source.

| Hours of Incubation | Residual Glucose (mg/ml) | | | L(+)-lactic acid formed (mg/ml) | | |
|---|---|---|---|---|---|---|
| | Flask A | Flask B | Flask C | Flask A | Flask B | Flask C |
| 0 | 21.58 | 21.58 | 21.58 | 0 | 0 | 0 |
| 4 | 19.42 | 18.46 | 18.71 | 2.23 | 2.23 | 1.74 |
| 24 | 17.82 | 13.23 | 11.92 | 3.46 | 8.14 | 6.88 |

Note:
Flask A-No pH control;
Flask B-pH control with 5% NaOH,
Flask C-pH control with 5% Ca(OH)$_2$ As evident from the table 2, when no pH was controlled, no significant increase in lactic acid production was observed, suggesting the growth cessation of *Paenibacillus macerans* IIPSP3 (MTCC 5569) at lower pH.

Though 5% NaOH showed a better performance than Ca(OH)$_2$, the selectivity towards targeted product (data not shown) was better when pH was maintained using Ca(OH)$_2$. Later, it was observed that the glucose consumption and lactic acid formation was better with CaCO$_3$ and so Ca(OH)$_2$ was further replaced with CaCO$_3$.

Example 4: Production of L-Lactic Acid Using Varying Concentration of Glucose

All the experimental conditions for the seed culture, production and analysis of end products were identical as mentioned in Example 1. However in the present experiment, varying concentrations of glucose were used ranging from 20 g/L to 80 g/L. The pH of 6.0 was maintained using 5% CaCO$_3$. Since no substantial increase in L (+) lactic acid production was observed after 48 hours as seen in Example 1, the present experiment was restricted to 72 hours only. Table 4 represents the percentage efficiency of the L-Lactic acid production based on initial glucose concentration at various time points.

Figure 2:
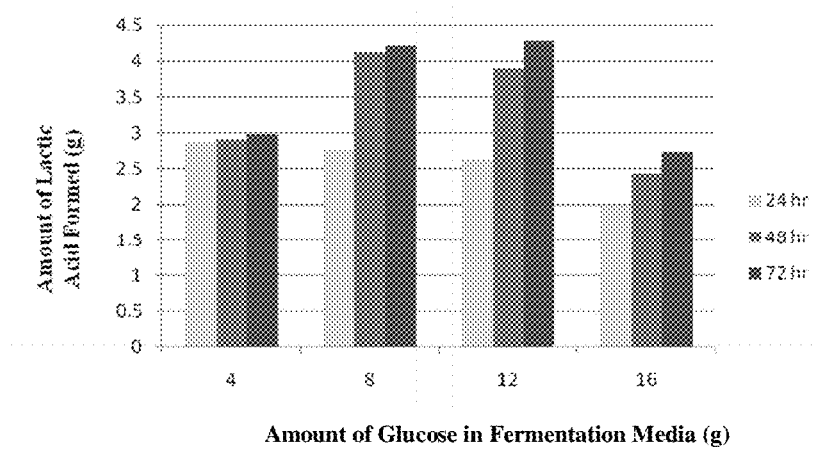
FIG. 2 shows the effect of initial glucose concentration on Lactic acid production by *Paenibacillus macerans* IIPSP3 (MTCC 5569) at different time points.

As evident from the FIG. 2, higher concentration of initial glucose was inhibitory for the production of L (+) lactic acid.

TABLE 4

Effect of increasing concentration on production efficiency of L-Lactic Acid by *Paenibacillus macerans* IIPSP3 (MTCC 5569) at different time points

| Initial glucose concentration (mg/ml) | L- Lactic Acid production Efficiency (%) from glucose at different time points | | |
|---|---|---|---|
| | 24 h | 48 h | 72 h |
| 20 | 71.65 | 72.82 | 74.28 |
| 40 | 34.47 | 51.6 | 52.7 |
| 60 | 21.97 | 32.48 | 35.6 |
| 80 | 12.31 | 15.1 | 17.1 |

Example 5: Screening of Carbon Sources Other than Glucose for L (+)-Lactic Acid Production All the experimental conditions for the seed culture, production and analysis of end products were identical as mentioned in Example 1. Various other carbon sources such as xylose, beechwood xylan, micro-crystalline cellulose, sodium salt of carboxymethyl cellulose, sulphonated lignin, cellobiose and acid pre-treated sugarcane bagasse pith were screened for lactic acid production. The pretreated sugarcane bagasse pith was obtained by treatment of sugarcane bagasse pith with 2% w/w Sulfuric acid with a holding time of 90 minutes at 140° C. This pretreatment resulted in hydrolysis of hemicellulose component in the form of liquid stream and cellulose and lignin rich biomass. Glucose fed flask served as a positive control. The concentration of all the carbon sources tested was 20 g/L.

The seed medium was prepared with glucose as sole carbon source. Since some of the carbon sources were complex, 3 ml of seed inoculum was transferred to 100 ml of autoclaved fermentation medium placed in 500 ml capacity Erlenmeyer flask. The samples were withdrawn after 24 hours and formation of lactic acid was assessed in supernatant centrifuged down at 10,000 rpm for 5 min at 4° C. using Hi-Plex H, HPLC column, with results shown in Table 5.

TABLE 5

Screening of various carbon sources (2%) for L-Lactic Acid production by *Paenibacillus macerans* IIPSP3 (MTCC 5569) after 24 hours

| Carbon Source | Lactic Acid Formed | Lactic Acid formed (mg/ml) | Other intermediate compounds detected |
|---|---|---|---|
| Xylose | + | 0.16 | — |
| Beechwood Xylan | − | Not detected | — |
| Microcrystalline Cellulose | ++ | 1.15 | — |
| CMC sodium salt | +++ | 3.64 | Glucose |
| Sulphonated Lignin | − | Not detected | — |
| Avicel PH 101 | ++ | 2.04 | Glucose |
| Acid pretreated Sugarcane bagasse pith | +++ | 2.86 | Glucose and Cellobiose |
| Cellobiose | ++++ | 10.16 | Glucose |
| Glucose (CONTROL) | ++++ | 18.10 | — |

Note:
(−) denotes absence of lactic acid;
(+) denotes lactic acid formed

As evident from the Table 5, the production of L(+) Lactic was found to be 1.15 mg/ml, 2.04 mg/ml, 3.64 mg/ml, and 2.86 mg/ml using 2% microcrystalline cellulose, Avicel PH 101, CMC sodium salt and acid pretreated sugarcane bagasse respectively as sole source of the carbon. Though no lactic acid production was observed in the flasks containing beechwood xylan and sulfonated lignin as sole carbon source, there was good growth of *Paenibacillus macerans* IIPSP3 (MTCC 5569) suggesting that the organism can also metabolise these complex carbon sources as well.

Example 6: Production of L(+) Lactic Acid Using Cellobiose as Substrate

Figure 3:
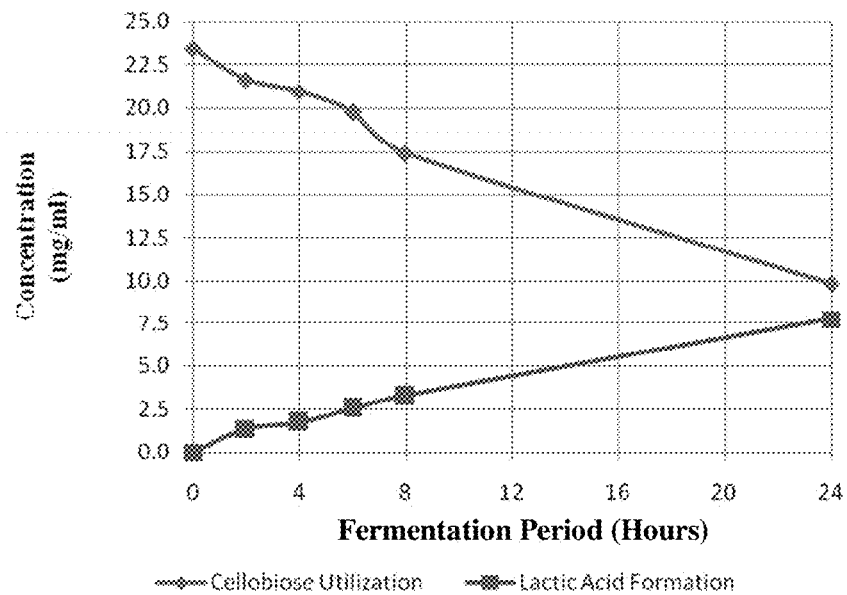
FIG. 3 shows trend of Cellobiose Consumption by *Paenibacillus macerans* IIPSP3 (MTCC 5569) for Lactic acid production.

All the experimental conditions for the seed culture, production and analysis of end products were identical as mentioned in Example 1. The seed medium was prepared with glucose as sole carbon source. 2 ml of seed inoculum was transferred to 100 ml of autoclaved fermentation medium with 2% Cellobiose as sole source of carbon, placed in 500 ml capacity Erlenmeyer flask. The samples were withdrawn aseptically under regular time intervals, maintaining the pH of the medium to 6.0. Formation of lactic acid was assessed in supernatant centrifuged down at 10,000 rpm for 5 min at 4° C. using Hi-Plex H, HPLC column, with results shown in FIG. 3.

There was a continuous increase in the L (+) Lactic Acid production up to 24 hours of fermentation when 2% cellobiose was used as a sole source of carbon (FIG. 2).

Example 7: Production of L-Lactic Acid Using 4% Acid Pre-Treated Sugarcane Pith Seed cultures of *Paenibacillus macerans* IIPSP3 (MTCC 5569) were grown aerobically at 50° C. in a liquid medium composed of 20 g/L glucose, 2 g/L yeast extract, 2 g/L ammonium sulphate in phosphate buffered medium (pH 7.2±0.3) containing 0.2 g/L $MgCl_2$ and 0.025 g/L $CaCl_2$. This medium was fortified with 2 ml/L of mineral solution containing trace metal namely 0.4 g/L $Na_2EDTA$, 0.34 g/L $MnSO_4.4H_2O$, 0.40 g/L $(NH_4)_6Mo_7O_{24}.4H_2O$, 0.8 g/L $FeSO_4.7H_2O$, 0.04 g/L $CoCl_2.6H_2O$, 0.02 g/L $NiCl_2.6H_2O$ and 0.02 g/L $ZnSO_4. 7H_2O$.

Mid-log aliquot of seed culture was inoculated (5%) to medium of similar composition except for the carbon source. The carbon source was 4% acid pretreated sugarcane pith (Glucan: 57%; Lignin: 36% and others: 7%). The pretreated sugarcane bagasse pith was obtained by treatment of sugarcane bagasse pith with 4% w/w Sulfuric acid with a holding time of 90 minutes at 140° C. This pretreatment resulted in hydrolysis of hemicellulose component in the form of liquid stream and cellulose and lignin rich biomass.

Lignin of the pre-treated bagasse was determined gravimetrically after hydrolyzing cellulose and hemicellulose fractions with sulphuric acid using NREL Laboratory Analytical Procedure. Sugars were analysed in the supernatant (NREL Standard Analytical Procedure #003) by High performance liquid chromatography using H-Plex H column from Agilent Technologies.

Unlike the glucose, which is a simpler carbon source, the pH drop started after $8^{th}$ hour. The pH was maintained above 5.8 using 5% $CaCO_3$ Samples were withdrawn after regular intervals and were subjected to HPLC analysis for lactic acid production. The result of the L-Lactic Acid produced from acid pretreated sugarcane bagasse has been shown in Table 6, wherein appreciable concentration of cellobiose and glucose was also detected.

TABLE 6

L-Lactic Acid production from 4% Acid -Pretreated sugar cane bagasse by *Paenibacillus macerans* IIPSP3 (MTCC 5569).

| Fermentation Period | Products formed during course of fermentation (mg/ml) | | |
|---|---|---|---|
| (h) | Cellobiose | Glucose | Lactic Acid |
| 0 | 0.97 | 0.58 | 0.00 |
| 14 | 0.98 | 0.32 | 1.38 |
| 16 | 0.92 | 0.38 | 1.20 |
| 18 | 0.83 | 0.25 | 1.00 |
| 24 | 0.34 | 0.00 | 0.17 |

As evident from table (6) above, a gradual drop in lactic acid concentration was observed after 14 hours, which may be possibly due to adsorption onto bagasse particles. The extraction and concentration of lactic acid can be initiated before its adsorption onto bagasse particles by extractive fermentation, a known process in state of art (A. Srivastava et al, *Biotechnol. Bioengg*, 1992; 39(6): 607-613).

Example 8: Production of L-Lactic Acid Using 2% Acid Pre-Treated Sugarcane Pith Seed cultures of *Paenibacillus macerans* IIPSP3 (MTCC 5569) were grown aerobically at 50° C. in a liquid medium composed of 20 g/L glucose, 2 g/L yeast extract, 2 g/L ammonium sulphate in phosphate buffered medium (pH 7.2±0.3) containing 0.2 g/L $MgCl_2$ and 0.025 g/L $CaCl_2$. This medium was fortified with 2 ml/L of mineral solution containing trace metal namely 0.4 g/L $Na_2EDTA$, 0.34 g/L $MnSO_4.4H_2O$, 0.40 g/L $(NH_4)_6Mo_7O_{24}.4H_2O$, 0.8 g/L $FeSO_4.7H_2O$, 0.04 g/L $CoCl_2.6H_2O$, 0.02 g/L $NiCl_2.6H_2O$ and 0.02 g/L $ZnSO_4. 7H_2O$.

Mid-log aliquot of seed culture was inoculated, (10%) to medium of similar composition except for the carbon source. The carbon source was 2% sugarcane pith (Biomass composition being Glucan: 42%; Lignin: 50% and others: 8%). The pretreated sugarcane bagasse pith was obtained by treatment of sugarcane bagasse pith with 2% w/w sulfuric acid with a holding time of 90 minutes at 140° C. This pretreatment resulted in hydrolysis of hemicellulose component in the form of liquid stream and cellulose and lignin rich biomass.

Figure 4:
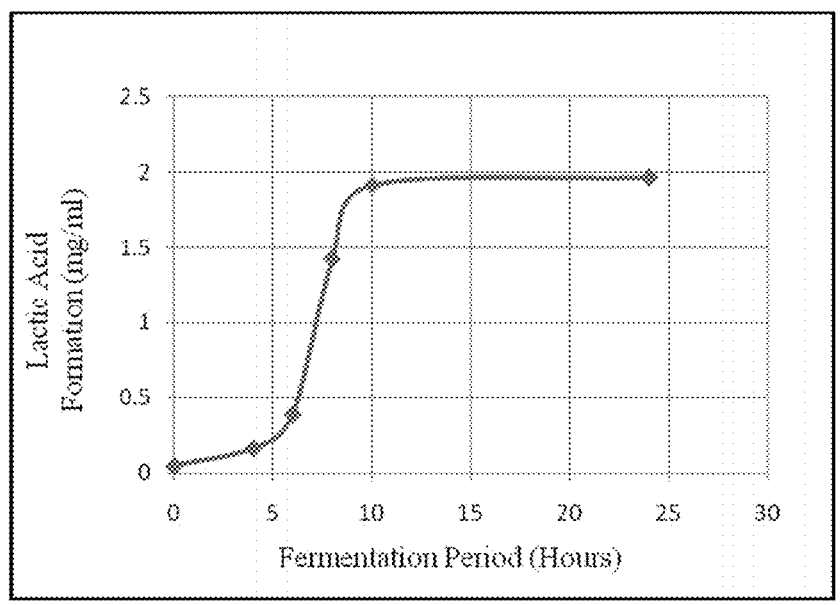
FIG. 4 shows course of L (+) Lactic Acid formation by *Paenibacillus macerans* IIPSP3 (MTCC 5569) from 2% Acid Pretreated Sugarcane Bagasse.

The composition of the cellulose rich biomass obtained after 4% sulphuric acid pretreatment was determined using NREL Laboratory Analytical procedure #003. Sugars were analysed in the supernatant by HPLC using H-Plex H column from Agilent Technologies. Table 7 represents glucose and L-lactic acid produced at different time points from 2% Acid pre-treated bagasse. FIG. 4 represents the course of formation of L(+) Lactic acid when 2% Acid pretreated sugarcane bagasse was used as sole source of carbon, before its entrapment in the bagasse particles.

TABLE 7

L-Lactic Acid production from 2% Acid -Pretreated sugar cane bagasse by *Paenibacillus macerans* IIPSP3 (MTCC 5569)

| Fermentation Period | Products formed from 2% Acid pretreated sugarcane bagasse during fermentation (mg/ml) | |
|---|---|---|
| (h) | Glucose | Lactic Acid |
| 0 | 1.46 | 0.05 |
| 4 | 1.57 | 0.166 |
| 6 | 0.76 | 0.394 |
| 8 | 1.27 | 1.434 |
| 10 | 1.18 | 1.920 |
| 24 | 1.08 | 1.971 |
| 32 | 0.35 | 0.631 |
| 48 | 0.39 | 0.722 |

At the end of 24 hours 1.97 mg/ml of L (+) Lactic acid was formed with 2% acid pretreated sugar cane bagasse. Unlike the glucose, which is a simpler carbon source, the pH drop started after $8^{th}$ hour. The pH was maintained above 5.8 using 5% $CaCO_3$. Samples were withdrawn after regular intervals and were subjected to HPLC analysis for lactic acid production.

No cellobiose was detected as evident from Table 7. In this experiment also as in Example 5, a significant drop in lactic acid concentration was observed after 24 hours, which may be possibly due to adsorption onto bagasse particles. However the extractive fermentation process can be followed to prevent losses of lactic acid onto bagasse.

Example 9: Effect of NaOH and CaCO₃ on Lactic Acid Productivity from 2% Acid Pretreated Bagasse All the conditions were same as in Example 6, but only to speed up the lactic acid production, 0.05% glucose was added in the main fermentation flask. The pH was maintained at 6.0 using two different neutralizing agents namely NaOH and $CaCO_3$ (concentration: 5%) and their effect was monitored for lactic acid productivity. The pH drop started from $4^{th}$ hour onwards with detectable CMC'ase activity of *Paenibacillus macerans* IIPSP3 (MTCC 5569). Table 8 shows the effect of two different neutralising agents on L-lactic acid productivity and the CMC'ase activity observed at different time points.

TABLE 8

Effect of neutralising agent on L-Lactic Acid production from 2% Acid Pretreated sugarcane bagasse by *Paenibacillus macerans* IIPSP3 (MTCC 5569)

| Fermentation Period (h) | Neutralizing agent | Lactic Acid (mg/ml) | Total CMC'ase Activity (U) |
|---|---|---|---|
| 0 | No | 0.026 | Not detected |
| 4 | NaOH | 2.26 | 31.5 |
| 6 | NaOH | 3.64 | 28.27 |
| 8 | NaOH | 3.06 | 30.13 |
| 4 | $CaCO_3$ | 2.17 | 27.76 |
| 6 | $CaCO_3$ | 3.27 | 34.99 |
| 8 | $CaCO_3$ | 2.93 | 35.18 |

Note:
The value of lactic acid shown at "0" hr indicates its derivation from seed medium.

At the end of 6 hours, when the pH was maintained with NaOH, a maximum of 3.64 mg/ml of L(+) lactic acid was produced with 28.27 Unit CMC'ase activity in the fermentation broth. Similarly when the pH was maintained with $CaCO_3$, a maximum of 3.27 mg/ml of L(+) lactic acid was produced with 34.99 Unit CMC'ase activity in the fermentation broth.

The endoglucanase assay was carried out by incubating the culture supernatant of appropriate dilution with 1 ml of 1% sodium salt of carboxymethyl cellulose (Fluka Grade-21902) dissolved in 50 mM acetate buffer (pH-4.8) at 50° C. for 10 min and terminating the assay with 3 ml DNS reagent. Colour development was done by boiling the reaction mixture for 5 minutes and readings were taken at 540 nm. Appropriate glucose standards were taken along with the substrate, reagent and enzyme blanks. CMC'ase activity may be defined as quantity of enzyme required to liberate 1 µmole of glucose/min under standard conditions. A maximum of 35.18 units of CMC'ase activity was observed in the supernatant after 8 hours of fermentation (Table 8).

No cellobiase/β glucosidase activity was detected in the supernatant suggesting that this specific enzyme may be membrane/cell bound or intracellular in nature. The same samples were subjected to HPLC analysis for lactic acid production.

ADVANTAGES OF THE INVENTION

1. Since this invention claims consolidated bio-processing of lignocellulosic biomass to L-lactic acid, no extra capital investment needs to be done as required in traditional methods such as separate hydrolysis and fermentation (SHF). The utility cost is also highly reduced in CBP process.
2. Up-scaling of the process is easier as the process does not require stringent conditions of anaerobicity.
3. As there is no or minimal requirement of enzyme from external sources, the operating cost of the process was reduced further.
4. Optically pure L (+) form of lactic acid is formed without any by-product contamination making downstream processing easier and cheaper.

REFERENCES

1. Hang (1990): Direct Fermentation of corn to L (+)-lactic acid by *Rhizopus oryzae*. U.S. Pat. No. 4,963,486.
2. S-P Tsai, S. H. Moon and R. Coleman (1995): Fermentation and recovery process for lactic acid production. U.S. Pat. No. 5,464,760.
3. Ohara H, and Y. Masahito (1996): Method of producing L-lactic acid with high optical purity using *Bacillus* strains. European Patent, EP0770684A2
4. K. Hofvendahl and B. Hahn-Hagerdal (2000): Factors affecting the fermentative lactic acid production from renewable resources. Enzyme and Microbial Technology; 26: 87-107.
5. Shin-ichiro Abe and Motoyoshi Takagi (1991): Simultaneous saccharification and fermentation of cellulose to lactic acid. Biotechnology and Bioengineering; 37: 93-96).
6. R. P. John, K. M. Nampoorthiri and Ashok Pandey (2008): L (+)-Lactic acid recovery from Cassava bagasse based fermentation medium using Anion exchange resins. Brazilian Archives of Biology and Technology; 51(6); 1241-1248.
7. Mark S. Ou, L. O. Ingram and K. T. Shanmugam (2011): L (+)-Lactic acid production from non-food carbohydrates by thermo tolerant *Bacillus coagulans*. Journal of Industrial Microbiology and Biotechnology; 38: 599-605.
8. Otto (2004): Preparation of lactic acid from a pentose containing substrate. PCT Application. International Patent Application Number: WO 2004/063382A2.
9. Otto (2004): Preparation of lactic acid from a pentose containing substrate. US Patent Application No. US2004/0203122A1.
10. G. Peter van Walsum, S. L. Walton, Adriaan Reinhard and P. Can Heiningen (2011): Production of lactic acid from hemicellulose extraction. US Patent Application No: US2011/0183389A1.
11. Svetlitchnyi, Vitaly and Curvers Simon (2013): Bioconversion of lignocellulosic biomass to Lactic acid. PCT Application No WO 2013/050584 A1.
12. M. Adsul, J. Khire, K. Bastawde and D. Gokhale (2007): Production of Lactic acid from cellobiose and cellotriose by *Lactobacillus delbrueckii* mutant Uc-3. Applied and Environmental Microbiology; 73(15): 5055-5057.
13. Mohamed Ali Abdel-Rahman, Y. Tashiro, T. Zendo, K. Shibata and K. Sonomoto (2011): Isolation and characterization of lactic acid bacterium for effective fermentation of cellobiose to optically pure homo L-(+)-lactic acid. Applied Microbiology and Biotechnology; 89: 1039-1049.
14. P. Dheeran, N. Nandhagopal, Sachin Kumar, Y. K. Jaiswal and D. K. Adhikari (2012): A novel thermostable xylanase of *Paenibacillus macerans* IIPS3 isolated from the termite gut. Journal of Industrial Microbiology and Biotechnology. DOI 10.1007/s10295-012-1093-1

15. A. Srivastava, P. K. Roychoudhary and V. Sahai (1992): Extractive Lactic Acid Fermentation using Ion-exchange resin. Biotechnology and Bioengineering; 39(6): 607-613.

16. A. Sluiter, B. Hames, R. Ruiz, C. Scarlata, J. Sluiter, D. Templeton, and D. Crocker (2008): Determination of structural carbohydrates and lignin in Biomass. Laboratory Analytical Procedure (*Technical Report* NREL/TP-510-42618), National Renewable Energy Laboratory (NREL), US Department of Energy Efficiency and Renewable Energy, Colorado US.

We claim:

1. A method of consolidated bioprocessing for production of L (+)-lactic acid and/or lactate comprising:
    a) providing a fermentation medium consisting of:
        a carbon source;
        ammonium sulphate;
        yeast extract;
        magnesium chloride;
        calcium chloride; and
        trace salts;
    b) inoculating the fermentation medium obtained in step a) with a microbial culture, wherein said microbial culture is a Gram positive thermophilic and cellulolytic bacterial isolate *Paenibacillus macerans* IIPSP3 (MTCC 5569);
    c) incubating said fermentation medium at a temperature in the range of 40° C. to 55° C.;
    d) adding sterile neutralizing agent to said fermentation medium during range of 4 to 8 hours of incubation to maintain pH of the medium in the range of about 5.5 to 7.2; and
    e) contacting said medium obtained in step a) with *Paenibacillus macerans* IIPSP3 (MTCC 5569) for a period of 6 to 48 hours for the production of L (+)-lactic acid and/or lactate.

2. The process as claimed in claim 1, wherein the carbon source is selected from the group consisting of lignocellulosic biomass, microcrystalline cellulose (MCC), sodium salt of carboxymethyl cellulose (CMC), beech wood xylan, a monosaccharide and a disaccharide.

3. The process as claimed in claim 2, wherein the lignocellulosic biomass is selected from the group consisting of agricultural residue, forest residue, herbaceous material, waste paper, paper, paper pulp, and paper mill residue.

4. The process as claimed in claim 3, wherein the agricultural residue is selected from the group consisting of bagasse obtained from sweet sorghum, bagasse obtained from sugarcane, residue from corn stover, residue from cotton stalks, residue from rice straw, and residue from wheat straw.

5. The process as claimed in claim 1, wherein the carbon source includes synthetic cellulosic substrates selected from the group consisting of Avicel PH-101, micro-crystalline cellulose, sodium salt of carboxymethyl cellulose, and hydrolysed products thereof that include cellobiose, or glucose.

6. The process as claimed in claim 1, wherein the trace salts are selected from the group consisting of $Na_2EDTA$, $MnSO_4.4H_2O$, $(NH_4)_6Mo_7O_{24}.4H_2O$, $FeSO_4.7H_2O$, $CoCl_2.6H_2O$, $NiCl_2.6H_2O$, and $ZnSO_4.7H_2O$.

7. The process as claimed in claim 1, wherein the neutralizing agent is selected from the group consisting of sodium hydroxide, calcium hydroxide, and calcium carbonate.

8. The process as claimed in claim 1, carried out in a single bioreactor under aerobic conditions and can be performed in batch and fed-batch conditions.

9. The process as claimed in claim 2, wherein the lignocellulosic biomass is contacted with *Paenibacillus macerans* IIPSP3 (MTCC 5569) for a period of 6 to 48 hours for the production of L (+)-lactic acid and/or lactate.

10. The process as claimed in claim 1, wherein no external enzymes are used.

11. The process of claim 2, wherein the monosaccharide or disaccharide comprises glucose, xylose or cellobiose.

* * * * *